United States Patent [19]
Conley et al.

[11] Patent Number: 6,063,582
[45] Date of Patent: May 16, 2000

[54] METHODS OF SCREENING FOR COMPOUNDS THAT INTERACT WITH HUMAN $P_{2U2}$ PURINERGIC RECEPTOR

[75] Inventors: Pamela B. Conley, Palo Alto; Hans-Michael Jantzen, San Francisco, both of Calif.

[73] Assignee: COR Therapeutics, Inc, South San Francisco, Calif.

[21] Appl. No.: 08/749,707

[22] Filed: Nov. 15, 1996

Related U.S. Application Data

[63] Continuation of application No. 08/559,524, Nov. 15, 1995, Pat. No. 5,871,963.
[60] Provisional application No. 60/006,782, Nov. 15, 1995.
[51] Int. Cl.$^7$ .......................... C12Q 1/00; C07K 14/705; C12N 15/12
[52] U.S. Cl. ..................... 435/7.21; 435/7.2; 435/69.1; 435/325; 435/348; 530/350; 536/23.5
[58] Field of Search ..................................... 435/7.2, 7.21, 435/325, 348, 69.1; 530/350; 536/23.5

[56] References Cited

U.S. PATENT DOCUMENTS 5,441,883  8/1995  Civelli et al. ...................... 435/257.13

OTHER PUBLICATIONS

Chang et al., Journal of Biological Chemistry, vol. 270, 26152–26158, Nov. 3,1995.

Tokuyama, Y., et al., "Cloning of Rat and Mouse P2y Purinoreceptors" *Biochemical and Biophysical Research Communications*, vol. 211, No. 1, Issue of Jun. 6, pp. 211–218 (1995).

Mohammed, Akbar G K, et al., "Identification Two Calcium–Signaling P2U Purinergic Recepptors in Human Erythro Leukemia Cells" *Experimental Biology*, Part 1, Issue of Apr. 9, pp. A117 (Abstract 684).

Conley,P. et al., "Cloning of a Novel Purinoreceptor from a Human Megacaryocytic Cell Line," *Blood*, 361a (Abstract 1433).

Kim et al., Characterization of the Purinergic P. Receptors in PC12 Cells, *Journal of Biological Chemistry*, vol. 269, No. 9, Issue of Mar. 4, pp. 6471–6477.

Lustig, et al., Expression cloning of an ATP receptor from mouse neuroblastoma cells, Proc. Nat'l Acad. Sci., USA, vol. 90, pp. 5113–5117, 1993.

Rice, et al., Cloning and Expression of the Alveolar Type II Cell $P_{2u}$ Purinergic Receptor, Am. J. Respir., Cell. Mol. Biol., vol. 12, pp. 27–32, 1995.

Webb, et al., Cloning and functional expression of a brain G–protein–coupled ATP receptor, FEBS, vol. 324, No. 2, 219–225, 1993.

Harden et al., *Am. Rev. Pharmacol. Toxicol.*, vol. 35, pp. 541–579 (1995).

Henderson et al., *Biochemical and Biophysical Research Comm.* vol. 212, pp. 648–656 (1995).

Parr et al., *Proc. Natl. Acad. Sci. USA*, vol. 91, pp. 3275–3279 (1994).

*Primary Examiner*—Sally P. Teng
*Attorney, Agent, or Firm*—Morgan, Lewis & Bockius LLP

[57] ABSTRACT

A novel subtype of the $P_2$-purinergic receptor, referred to as the $P_{2U2}$ receptor, is disclosed. This receptor is activated by four of its agonists in the following order of specificity: UTP>UDP>ADP>ATP. Nucleic acids encoding the receptor and associated screening and therapeutic methods also are disclosed.

12 Claims, 5 Drawing Sheets

```
ATAAAGTATG TTTAGCCCTC ATGTCACATG AACCTTTATG CATTGAAGAT    50
TGTTTCCCTT GCCCCCCCAG GGGGTGGGGT TATTTTTCTA TCCTTGTTAA   100
CTTCCCTATA TTATTATATA CACTTTGAGT TTTAGGGTAC ATGTGCACAA   150
AGTGCAGGTT AGTTACATAT GTATACATGT GCCATGTTGG TGTGCTGCAC   200
CCATTAACAC ATCATTTAGC ATGAGGTATA TCTCCTAATG TTATCCCTCC   250
CCCCTCCCCC CACCCCACAA CAGTCCCCGG AGTGTGATAT TCCCCTTTCC   300
TGTGTCCATG TGTTATTATT CCAATTCCCC ACCTATGAAG TGAAAATATG   350
CAGGTGTTTG GATTTTGTC CTTGGCAATA GTTTTGCTGA GAATGATGGT    400
TTCCAGCTTC ATCCATGTCC CTACAAGGA CATGAACTCA TCATTTTTA     450
TGACTGCATA GTATTCTATG GTGTATACAT GCCAACTTTT CTCCCCCCCC   500
TTTTTAAGCT CCTTCTTTCA CTGGCTTTCA TGATCCCACC AATTCCTGCT   550
TTTCCTTTTT TGTTTTTTTC TTCCAACAGA ATGGTTATGG TTTAACTCAG   600
CAGAATTTGT TGAACAACTA CGACATGCTG GGGATCATGG CATGGAATGC   650
                                  M  L  G  I  M  A  W  N  A

AACTTGCAAA AACTGGCTGG CAGCAGAGGC TGCCCTGGAA AAGTACTACC   700
 T  C  K  N  W  L  A   A  E  A    A  L  E   K  Y  Y  L
                          I
TTTCCATTTT TTATGGGATT GAGTTCGTTG TGGGAGTCCT TGGAAATACC   750
 S  I  F   Y  G  I    E  F  V  V   G  V  L   G  N  T

ATTGTTGTTT ACGGCTACAT CTTCTCTCTG AAGAACTGGA ACAGCAGTAA   800
 I  V  V  Y   G  Y  I   F  S  L   K  N  W  N   S  S  N
                                              II
TATTTATCTC TTTAACCTCT CTGTCTCTGA CTTAGCTTTT CTGTGCACCC   850
 I  Y  L   F  N  L  S   V  S  D   L  A  F    L  C  T  L

TCCCCATGCT GATAAGGAGT TATGCCAATG GAAACTGGAT ATATGGAGAC   900
 P  M  L    I  R  S    Y  A  N  G  N  W  I   Y  G  D

GTGCTCTGCA TAAGCAACCG ATATGTGCTT CATGCCAACC TCTATACCAG   950
 V  L  C  I   S  N  R   Y  V  L   H  A  N  L   Y  T  S
```

FIG. 1A

```
                    III
CATTCTCTTT CTCACTTTTA TCAGCATAGA TCGATACTTG ATAATTAAGT  1000
  I  L  F   L  T  F  I   S  I  D    R  Y  L    I  I  K  Y

ATCCTTTCCG AGAACACCTT CTGCAAAAGA AAGAGTTTGC TATTTTAATC  1050
  P  F  R    E  H  L    L  Q  K  K    E  F  A    I  L  I
                              IV
TCCTTGGCCA TTTGGGTTTT AGTAACCTTA GAGTTACTAC CCATACTTCC  1100
 S  L  A  I   W  V  L   V  T  L   E  L  L  P   I  L  P

CCTTATAAAT CCTGTTATAA CTGACAATGG CACCACCTGT AATGATTTTG  1150
  L  I  N    P  V  I    T  D  N  G    T  T  C    N  D  F  A

CAAGTTCTGG AGACCCCAAC TACAACCTCA TTTACAGCAT GTGTCTAACA  1200
  S  S  G    D  P  N    Y  N  L  I    Y  S  M    C  L  T
                             V
CTGTTGGGGT TCCTTATTCC TCTTTTTGTG ATGTGTTTCT TTTATTACAA  1250
 L  L  G    F  L  I  P   L  F  V    M  C  F  F    Y  Y  K

GATTGCTCTC TTCCTAAAGC AGAGGAATAG GCAGGTTGCT ACTGCTCTGC  1300
  I  A  L    F  L  K  Q   R  N  R   Q  V  A    T  A  L  P

CCCTTGAAAA GCCTCTCAAC TTGGTCATCA TGGCAGTGGT AATCTTCTCT  1350
   L  E  K   P  L  N    L  V  I  M    A  V  V    I  F  S
 VI
GTGCTTTTTA CACCCTATCA CGTCATGCGG AATGTGAGGA TCGCTTCACG  1400
 V  L  F  T   P  Y  H    V  M  R    N  V  R  I    A  S  R

CCTGGGGAGT TGGAAGCAGT ATCAGTGCAC TCAGGTCGTC ATCAACTCCT  1450
  L  G  S    W  K  Q  Y   Q  C  T    Q  V  V    I  N  S  F
                                                      VII
TTTACATTGT GACACGGGCT TTGGGCTTTC TGAACAGTGT CATCAACCCT  1500
   Y  I  V   T  R  A    L  G  F  L   N  S  V    I  N  P

GTCTTCTATT TTCTTTTGGG AGATCACTTC AGGGACATGC TGATGAATCA  1550
 V  F  Y  F   L  L  G    D  H  F    R  D  M  L    M  N  Q

ACTGAGACAC AACTTCAAAT CCCTTACATC CTTTAGCAGA TGGGCTCATG  1600
  L  R  H    N  F  K  S   L  T  S    F  S  R    W  A  H  E

AACTCCTACT TTCATTCAGA GAAAAGTGAG GGGCTTGTGA AACAGATTGT  1650
  L  L  L    S  F  R    E  K

TCTACAGATG AATCTGTAAG CCAGTTACAG TTTGCTTTAA CTCATAGACA  1700

TCAATCAGAG AGTGTCACAG ATTTAACCTT GATCTAAAGA CAAGTTGTAC  1750
```

FIG. 1B

```
CCAGAGTATG TGAAAAGAAT GGGACGACAA GAATGTACTG GTTTCTTCCT   1800
CTAAGAATTG AAAGGAGTTG AACTGCCTTA TGTTTGGGCA TGTAACTCCA   1850
AAATACTAGG TAGTATAAGG CTTTCTCAAT CAGTCCCCAA ATGGAAGATA   1900
TATAAAGCAA CAAGTTGTCT GCATTTGATC ACTGGTCAGA TTGTAAAAAA   1950
AAAAAAAAAA AAGGGCGNCC GCCACCGCGG TGGAGCTCCA ATCGCC      1996
```

METHODS OF SCREENING FOR COMPOUNDS THAT INTERACT WITH HUMAN P$_{2U2}$ PURINERGIC RECEPTOR

CROSS-REFERENCES TO RELATED APPLICATIONS

This application claims priority to Provisional Application Ser. No. 60/006,782, filed Nov. 15, 1995. This application is also a continuation of U.S. application Ser. No. 08/559,524, filed Nov. 15, 1995, which issued as U.S. Pat. No. 5,871,963 on Feb. 16, 1999.

FIELD OF THE INVENTION

The present invention relates to a new subtype of the P$_2$-Purinergic receptors, which is abundantly expressed in kidney and in many cell lines of megakaryocytic or erythroleukemic origin. Referred to herein as the P$_{2U2}$ receptor, this receptor is activated by ATP, ADP, UTP and UDP. The P$_{2U2}$ receptor can be used as a tool to screen for agonists and antagonists that can either stimulate or block receptor activation. Such compounds have therapeutic utility in treating (1) diseases that are caused by aberrant activation of this receptor, for example over stimulation or under stimulation of the receptor and (2) diseases whose symptoms can be ameliorated by stimulating or inhibiting the activity of the P$_{2U2}$ receptor.

The present invention also relates to the isolated entire human gene encoding the P$_{2U2}$ receptor, methods for the recombinant production of purified P$_{2U2}$ receptor proteins and the proteins made by these methods, antibodies against the whole P$_{2U2}$ receptor or regions thereof, vectors, nucleotide probes, and host cells transformed by genes encoding polypeptides having the P$_{2U2}$ receptor activity, along with diagnostic and therapeutic uses for these various reagents.

BACKGROUND OF THE INVENTION

Purinergic receptors are cell surface receptors that interact with extracellular adenine or uridine nucleotides and nucleosides. These receptors are present throughout the central nervous system and peripheral tissues and play a role in numerous physiological responses.

The purinergic receptors are broadly divided into two major receptor types, P$_1$ and P$_2$, which are defined by their level of interaction with the adenine nucleotides and nucleosides. Where P$_1$ receptors are activated by adenosine and exhibit a potency order of adenosine>AMP>ADP>ATP, P$_2$ receptors are activated by ATP, UTP, ADP or UDP and exhibit a potency order of ATP$\geq$ADP>AMP>adenosine. As more has become known about the purinergic receptors and the wide range of physiological responses in which they play a role, the P$_1$- and P$_2$-type classifications were no longer sufficient to accurately portray this complex family of receptors. Therefore, receptor subtype categories have been developed. For example, the P$_2$-type purinergic receptors are now classified as P$_{2Y}$-, P$_{2U}$-, P$_{2T}$-, P$_{2X}$- and P$_{2Z}$-subtypes. A review of the P$_2$-type purinergic receptors can be found in Harden, et al, *Ann. Rev. Pharmacol. Toxicol.* 35:541–579 (1995).

Classification of the P$_2$-type purinergic receptors has been difficult because there are no published selective P$_2$-receptor antagonists and there are few ATP or ADP receptor-subtype specific agonists. In addition, it has been difficult to compare the relative order of potency of P$_2$-purinergic receptor agonists. Hence, this subtype has presented numerous challenges in the identification and characterization of its members.

SUMMARY OF THE PRESENT INVENTION

One aspect of the invention is an isolated and purified polypeptide comprising the amino acid sequence of FIG. 1 (SEQ ID NO:2).

Another aspect of the invention is an isolated and purified nucleic acid sequence encoding for the P$_{2U2}$ receptor.

Yet another aspect of the invention is an isolated and purified nucleic acid sequence comprising the nucleotide sequence of FIG. 1 (SEQ ID NO:1).

BRIEF DESCRIPTION OF THE DRAWINGS

FIG. 1A–FIG. 1C is the DNA (SEQ ID NO:1) and deduced amino acid sequence (SEQ ID NO:2) of the human P$_{2U2}$ receptor.

FIG. 2 is a comparison of the amino acid sequence (SEQ ID NO:2) of the human P$_{2U2}$ receptor with the amino acid sequence of the human P$_{2U}$ receptor (Parr, et al., *Proc. Natl. Acad. Sci. USA* 91:3275–3279 (1994)) (SEQ ID NO:3) and the bovine P$_2$Y$_1$ receptor (Henderson, et al. *BBRC* 212:648–656 (1995) (SEQ ID NO:4). The Parr P$_{2U}$ receptor is referred to in FIG. 2 as "P$_{2U1}$".

DESCRIPTION OF THE PREFERRED EMBODIMENTS

Figure 3:
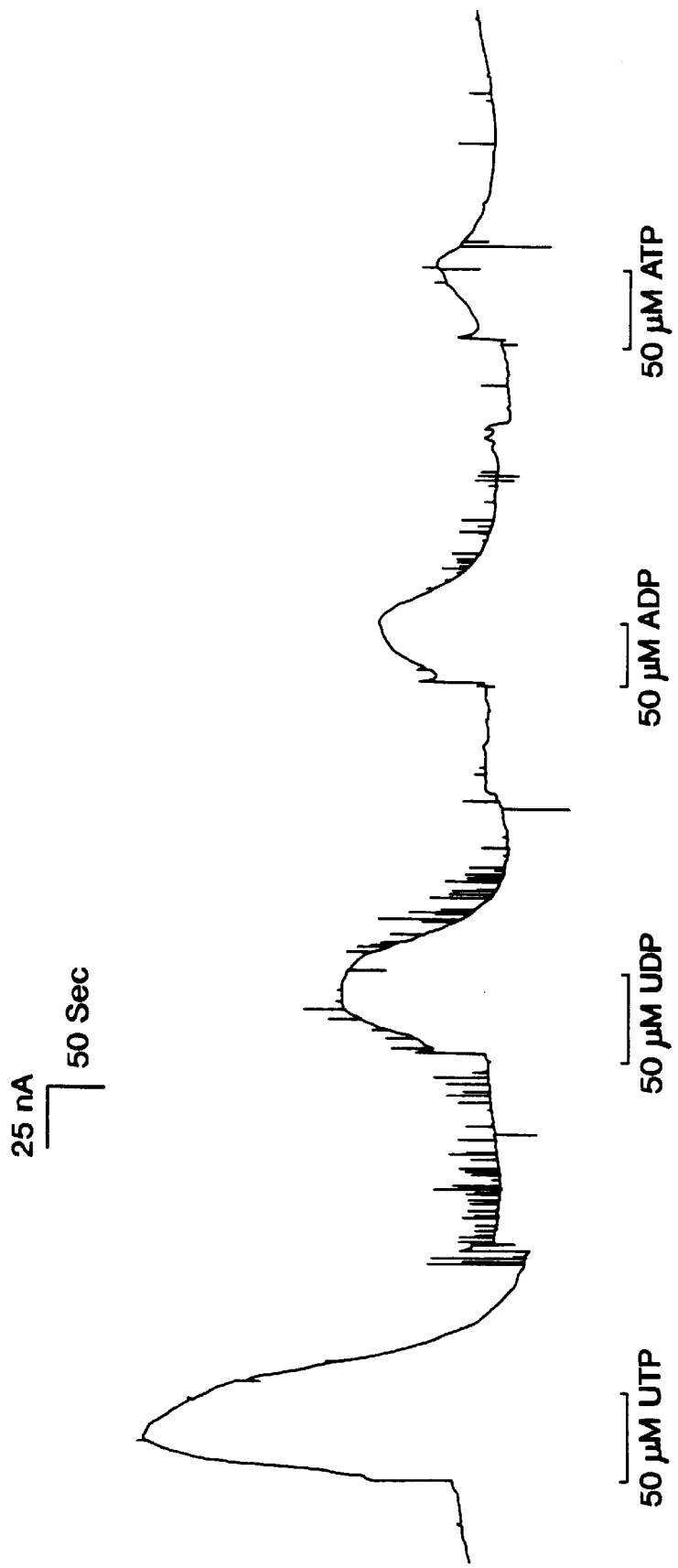
FIG. 3 shows representative chloride currents obtained from oocytes injected with cRNA for the receptor and challenged with a variety of purinergic agonists (ADP, ATP, UTP, UDP).

The present invention provides methods and materials useful in the regulation of the renal system in mammals. Recent studies provide evidence that extracellular nucleotides influence the renal microvasculature. See Inscho, et al., *FASEB Journal* 8:319–328 (1994). The isolation, recombinant production and characterization of the purinergic receptor of the invention allows for the effective regulation of these functions.

Before proceeding further with a description of the specific embodiments of the present invention, a number of terms will be defined.

The terms "substantially pure" and "isolated" are used herein to describe a protein that has been separated from the native contaminants or components that naturally accompany it. Typically, a monomeric protein is substantially pure when at least about 60 to 70% of a sample exhibits a single polypeptide backbone. Minor variants or chemical modifications typically share approximately the same polypeptide sequence. A substantially pure protein will typically comprise over about 85 to 90% of a protein sample, preferably will comprise at least about 95%, and more preferably will be over about 99% pure. Purity is typically measured on a polyacrylamide gel, with homogeneity determined by staining. For certain purposes, high resolution will be desired and HPLC or a similar means for purification utilized. However, for most purposes, a simple chromatography column or polyacrylamide gel will be used to determine purity. Whether soluble or membrane bound, the present invention provides for substantially pure preparations. Various methods for their isolation from biological material may be devised, based in part upon the structural and functional descriptions contained herein. In addition, a protein that is chemically synthesized or synthesized in a cellular system that is different from the cell from which it naturally originates, will be substantially pure. The term is also used to describe receptors and nucleic acids that have been synthesized in heterologous mammalian cells or plant cells, *E. coil* and other prokaryotes.

As used herein, the terms "hybridization" (hybridizing) and "specificity" (specific for) in the context of nucleotide sequences are used interchangeably. The ability of two nucleotide sequences to hybridize to each other is based upon a degree of complementarity of the two nucleotide sequences, which in turn is based on the fraction of matched complementary nucleotide pairs. The more nucleotides in a given sequence that are complementary to another sequence, the greater the degree of hybridization of one to the other. The degree of hybridization also depends on the conditions of stringency which include temperature, solvent ratios, salt concentrations, and the like. In particular, "selective hybridzation" pertains to conditions in which the degree of hybridization of a polynucleotide of the invention to its target would require complete or nearly complete complementarity. The complementarity must be sufficiently high so as to assure that the polynucleotide of the invention will bind specifically to the target relative to binding other nucleic acids present in the hybridization medium. With selective hybridization, complementarity will be 90–100%, preferably 95–100%, more preferably 100%.

The present invention relates to a new purinergic receptor of the $P_2$ subclass, which is referred to herein as the $P_{2U2}$ receptor. FIG. 1A–FIG. 1C (SEQ ID NO:1) shows the DNA sequence of the clone encoding the $P_{2U2}$ receptor along with the deduced amino acid sequence. The amino acid sequence shown in FIG. 1A–FIG. 1C (SEQ ID NO:1) includes four putative extracellular domains (the $NH_2$-terminus and ECD I–ECD III) and seven putative transmembrane regions (TM I–TM VII). As used herein, the "$P_{2U2}$ receptor" refers to the receptor in any animal species sharing a common biological activity with the human receptor contained in the clone described in Example 1 herein. This "common biological activity" includes but is not limited to an effector or receptor function or cross-reactive antigenicity. Using the native DNA encoding the human form of this receptor, the $P_{2U2}$ receptors in other species, may be obtained.

Because the $P_{2U2}$ receptor is activated by UTP, it is classified as a $P_2$-type purinergic receptor. Hydrophobicity/hydrophilicity plots of the $P_{2U2}$ receptor sequence shown in FIG. 1A–FIG. 1C (SEQ ID NO:1) suggest that the $P_{2U2}$ receptor has 7 putative transmembrane domains. This, along with the following characteristics, are consistent with characteristics that are observed in other $P_2$-type purinergic receptors:

seven putative α-helical transmembrane-spanning structures;

amino terminus located on the extracellular side of the membrane;

carboxy terminus located on the intracellular side of the membrane; and conservation of sequence in the transmembrane spanning domains as compared with other $P_2$-purinergic receptors.

It has been found that the $P_{2U2}$ receptor is expressed in many cell lines of megakaryocytic or erythroleukemic origin. In addition, the $P_{2U2}$ receptor is expressed, at the RNA level, predominantly in the kidney. This receptor is unusual in that, although most purinergic receptors are present in the brain, the $P_{2U2}$ receptor has not been found to be expressed in human brain tissue. The tissue distribution of the $P_{2U2}$ receptor is described in Example 3.

Some $P_2$ receptors have a strong preference for one nucleotide. Alternately, they may be activated by several nucleotides but the specificity for one nucleotide is usually an order of magnitude greater than for the other nucleotides. The $P_{2U2}$ receptor is activated by ATP, ADP, UTP and UDP when expressed in *Xenopus oocytes,* with the following order of specificity:

UTP>UDP>ADP>ATP

However, unlike for other $P_2$ receptors, the potency of ATP, ADP, UTP and UDP as agonists for the $P_{2U2}$ receptor are close in value, with a mere five-fold differences.

One aspect of the present invention also relates to the human gene encoding the $P_{2U2}$ receptor, which has both diagnostic and therapeutic uses as are described below. Included within this invention are proteins or peptides having substantial homology with the amino acid sequence of FIG. 1A–FIG. 1C (SEQ ID NO:1).

Ordinarily, the $P_{2U2}$ receptors and analogs thereof claimed herein will have an amino acid sequence having at least 75% amino acid sequence identity with the $P_{2U2}$ receptor sequence disclosed in FIG. 1A–FIG. 1C (SEQ ID NO:1), more preferably at least 80%, even more preferably at least 90%, and most preferably at least 95%. Identity or homology with a sequence is defined herein as the percentage of amino acid residues in the candidate sequence that are identical with the sequence of the $P_{2U2}$ receptor, after aligning the sequences and introducing gaps, if necessary, to achieve the maximum percent homology, and not considering any conservative substitutions as part of the sequence identity. None of N-terminal, C-terminal or internal extensions, deletions, or insertions of the $P_{2U2}$ receptor sequence shall be construed as affecting homology.

Thus, the claimed $P_{2U2}$ receptor and analog molecules that are the subject of this invention include molecules having the $P_{2U2}$ receptor amino acid sequence; fragments thereof having a consecutive sequence of at least 10, 15, 20, 25, 30 or 40 amino acid residues from the $P_{2U2}$ receptor sequence of FIG. 1A–FIG. 1C (SEQ ID NO:1); amino acid sequence variants of the $P_{2U2}$ receptor sequence of FIG. 1A–FIG. 1C (SEQ ID NO:1) wherein an amino acid residue has been inserted N- or C-terminal to, or within, (including parallel deletions) the $P_{2U2}$ receptor sequence or its fragments as defined above; amino acid sequence variants of the $P_{2U2}$ receptor sequence of FIG. 1A–FIG. 1C (SEQ ID NO:1) or its fragments as defined above which have been substituted by at least one residue.

$P_{2U2}$ receptor polypeptides include those containing predetermined mutations by, e.g., homologous recombination, site-directed or PCR mutagenesis, and $P_{2U2}$ receptor polypeptides of other animal species, including but not limited to rabbit, rat, murine, porcine, bovine, ovine, equine and non-human primate species, and alleles or other naturally occurring variants of the $P_{2U2}$ receptor of the foregoing species and of human sequences; derivatives of the commonly known $P_{2U2}$ receptor or its fragments wherein the $P_{2U2}$ receptor or its fragments have been covalently modified by substitution, chemical, enzymatic, or other appropriate means with a moiety other than a naturally occurring amino acid (for example a detectable moiety such as an enzyme or radioisotope); glycosylation variants of the $P_{2U2}$ receptor (insertion of a glycosylation site or deletion of any glycosylation site by deletion, insertion or substitution of appropriate amino acid); and soluble forms of the $P_{2U2}$ receptor. This invention also includes tagging the $P_{2U2}$ receptor, in particular for use in purification or diagnostic application. Types and methods of tagging are well known in the art, for example, the use of hexa-histidine tags.

Most sequence modifications, including deletions and insertions, and substitutions in particular, are not expected to produce radical changes in the characteristics of the $P_{2U2}$ receptor. However, when it is difficult to predict the exact effect of the sequence modification in advance of making the change, one skilled in the art will appreciate that the affect of any sequence modification will be evaluated by routine screening assays.

$P_{2U2}$ receptor peptides may be purified using techniques of classical protein chemistry, such as are well known in the art. For example, a lectin affinity chromatography step may be used, followed by a highly specific ligand affinity chromatography procedure that utilizes a ligand conjugated to biotin through the cysteine residues of the ligand. Alternately, a hexa-histidine tagged receptor may be purified using nickel column chromatography.

The nomenclature used to describe the peptide compounds of the invention follows the conventional practice where the N-terminal amino group is assumed to be to the left and the carboxy group to the right of each amino acid residue in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal $H^+_2$ and C-terminal $O^-$ at physiological pH are understood to be present though not necessarily specified and shown, either in specific examples or in generic formulas. Free functional groups on the side chains of the amino acid residues can also be modified by amidation, acylation or other substitution, which can, for example, change the solubility of the compounds without affecting their activity.

In the peptides shown, each gene-encoded residue, where appropriate, is represented by a single letter designation, corresponding to the trivial name of the amino acid, in accordance with the following conventional list:

| Amino Acid | One Letter Symbol | Three-letter |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The amino acids not encoded genetically are abbreviated as indicated in the discussion below.

In the specific peptides shown in the present application, the L-form of any amino acid residue having an optical isomer is intended unless the D-form is expressly indicated by a dagger superscript (-†). This invention also contemplates non-naturally occurring amino acids (typically those which are not naturally encoded) as are well known in the art.

The compounds of the invention are peptides which are partially defined in terms of amino acid residues of designated classes. Amino acid residues can be generally subclassified into four major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows:

Acidic: Aspartic acid and Glutamic acid

Basic/noncyclic: Arginine and Lysine

Basic/cyclic: Histidine

Neutral/polar/small: Glycine, serine and cysteine

Neutral/nonpolar/small: Alanine

Neutral/polar/large/nonaromatic: Threonine, Asparagine and Glutamine

Neutral/polar/large aromatic: Tyrosine

Neutral/nonpolar/large/nonaromatic: Valine, Isoleucine, Leucine and Methionine

Neutral/nonpolar/large/aromatic: Phenylalanine, and Tryptophan

The gene-encoded secondary amino acid proline, although technically within the group neutral/nonpolar/large/cyclic and nonaromatic, is a special case due to its known effects on the secondary conformation of peptide chains, and is not, therefore, included in this defined group.

Certain commonly encountered amino acids, which are not encoded by the genetic code, include, for example, beta-alanine (beta-Ala), or other omega-amino acids, such as 3-amino propionic, 2,3-diamino propionic (2,3-diaP), 4-amino butyric and so forth, alpha-aminisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) 2-naphthylalanine (2-Nal); 1,2,3,4-tetrahydroisoquinoline-3-carboxylic acid (Tic); β-2-thienylalanine (Thi); and methionine sulfoxide (MSO). These also fall conveniently into particular categories.

Based on the above definitions,

Sar, beta-Ala, 2,3-diaP and Aib are neutral/nonpolar/small;

t-BuA, t-BuG, N-MeIle, Nle, Mvl and Cha are neutral/nonpolar/large/nonaromatic;

Orn is basic/noncyclic;

Cya is acidic;

Cit, Acetyl Lys, and MSO are neutra/polar/large/nonaromatic; and

Phg, Nal, Thi and Tic are neutra/nonpolar/large/aromatic.

The various omega-amino acids are classified according to size as neutra/nonpolar/small (beta-Ala, i.e., 3-aminopropionic, 4-aminobutyric) or large (all others).

Other amino acid substitutions of those encoded in the gene can also be included in peptide compounds within the scope of the invention and can be classified within this general scheme according to their structure.

All of the compounds of the invention, when an amino acid forms the C-terminus, may be in the form of the pharmaceutically acceptable salts or esters. Salts may be, for example, $Na^+$, $K^+$, $Ca^{+2}$, $Mg^{+2}$ and the like; the esters are generally those of alcohols of 1–6C.

In all of the peptides of the invention, one or more amide linkages (—CO—NH—) may optionally be replaced with another linkage which is an isostere such as —CH$_2$NH—, —CH$_2$S—, —CH$_2$CH$_2$—, —CH=CH— (cis and trans), —COCH$_2$—, —CH(OH)$_2$— and —CH$_2$SO—. This replacement can be made by methods known in the art. The following references describe preparation of peptide analogs which include these alternative-linking moieties: Spatola, *Vega Data* 1(3) "Peptide Backbone Modifications" (general review) (March 1983); Spatola, in "Chemistry and Biochemistry of Amino Acids Peptides and Proteins," B. Weinstein, eds., Marcel Dekker, New York, p. 267 (1983) (general review); Morley, J. S., *Trends Pharm Sci.* pp. 463–468 (general review) (1980); Hudson, et al., *Int J Pept Prot Res* 14:177–185 (—CH$_2$NH—, —CH$_2$CH$_2$—) (1979); Spatola, et al., *Life Sci* 38:1243–1249 (—CH$_2$—S) (1986); Hann, *J Chem Soc Perkin Trans I* 307–314 (—CH—CH—, cis and trans) (1982); Almquist, et al., *J Med Chem* 23:1392–1398 (—COCH$_2$—) (1980); Jennings-White, et al., *Tetrahedron Lett* 23:2533 (—COCH$_2$—) (1982); Szelke, et al., European Application EP 45665 (1982) CA:97:39405 (1982) (—CH(OH)CH$_2$—); Holladay, et al., *Tetrahedron Lett* 4:4401–4404 (—C(OH)CH$_2$—) (1983); and Hruby, *Life Sci.* 31:189–199 (—CH$_2$—S—) (1982).

The invention provides methods and materials useful in assay systems to determine the ability of candidate pharmaceuticals to affect the activity of the $P_{2U^2}$ receptor. The isolation, recombinant production and characterization of the $P_{2U^2}$ receptor allows for the design of assay systems using the $P_{2U^2}$ receptor as a substrate and using agonists and antagonists for the receptor as control reagents in the assay.

One embodiment of the invention relates to recombinant materials associated with the production of the $P_{2U2}$ receptor. These include transfected cells that can be cultured so as to display or express the $P_{2U2}$ receptor on its surface, thus providing an assay system for the interaction of materials with the native $P_{2U^2}$ receptor where these cells or relevant fragments of the $P_{2U2}$ receptor are used as a screening tool to evaluate the effect of various candidate compounds on the $P_{2U2}$ receptor activity in vivo, as is described below. Suitable cells include Xenopus oocytes and most mammalian cell lines.

Recombinant production of the $P_{2U2}$ receptor involves using a nucleic acid sequence that encodes the $P_{2U2}$ receptor, as is set forth in FIG. 1A–FIG. 1C (SEQ ID NO:1), or its degenerate analogs. The nucleic acid can be prepared either by retrieving the native sequence, as described below, or by using substantial portions of the known native sequence as a probe, or it can be synthesized de novo using procedures that are well known in the art.

The nucleic acid may be ligated into expression vectors suitable for the desired host and then transformed into compatible cells. Alternatively, nucleic acids may be introduced directly into a host cell by techniques such as are well known in the art. The cells are cultured under conditions favorable for the expression of the gene encoding the $P_{2U2}$ receptor and cells displaying the receptor on the surface are then harvested. Suitable cells include *E. coli*, Chinese Hamster Ovary cells, human Jurkat T-cell line, the rat-2 fibroblast cell line, human astocytoma 1321N1 cell line and insect cell lines such as Sf-9.

This invention also relates to nucleic acids that encode or are complementary to a $P_{2U2}$ receptor polypeptide. These nucleic acids can then be used to produce the polypeptide in recombinant cell culture for diagnostic use or for potential therapeutic use. In still other aspect, the invention provides an isolated nucleic acid molecule encoding a $P_{2U2}$ receptor, either labeled or unlabeled, or a nucleic acid sequence that is complementary to, or hybridizes under stringent conditions to, a nucleic acid sequence encoding a $P_{2U2}$ receptor. The isolated nucleic acid molecule of the invention excludes nucleic acid sequences which encode, or are complementary to nucleic acid sequences encoding, other known purinergic receptors which are not $P_{2U2}$ receptors, such as the human $P_{2U}$, and the chicken and bovine $P_{2Y1}$ receptors, and the like.

This invention also provides a replicable vector comprising a nucleic acid molecule encoding a $P_{2U2}$ receptor operably linked to control sequences recognized by a host transformed by the vector; host cells transformed with the vector; and a method of using a nucleic acid molecule encoding a $P_{2U2}$ receptor to effect the production of a $P_{2U2}$ receptor on the cell surface, comprising expressing the nucleic acid molecule in a culture of the transformed host cells and recovered from the cells. The nucleic acid sequence is also useful in hybridization assays for $P_{2U2}$ receptor-encoding nucleic acid molecules.

In still further embodiments of the invention, a method is described for producing $P_{2U2}$ receptors comprising inserting into the DNA of a cell containing the nucleic acid sequence encoding a $P_{2U2}$ receptor a transcription modulatory element (such as an enhancer or a silencer) in sufficient proximity and orientation to the $P_{2U2}$ receptor coding sequence to influence transcription thereof, with an optional further step comprising culturing the cell containing the transcription modulatory element and the $P_{2U2}$ receptor-encoding nucleic acid sequence.

This invention also covers a cell comprising a nucleic acid sequence encoding a $P_{2U2}$ receptor and an exogenous transcription modulatory element in sufficient proximity and orientation to the above coding sequence to influence transcription thereof and a host cell containing the nucleic acid sequence encoding a $P_{2U2}$ receptor operably linked to exogenous control sequences recognized by the host cell.

This invention provides a method for obtaining cells having increased or decreased transcription of the nucleic acid molecule encoding a $P_{2U2}$ receptor, comprising: providing cells containing the nucleic acid molecule; introducing into the cells a transcription modulating element; and screening the cells for a cell in which the transcription of the nucleic acid molecule is increased or decreased.

$P_{2U2}$ receptor nucleic acids for use in the invention can be produced as follows. A $P_{2U2}$ receptor "nucleic acid" is defined as RNA or DNA that encodes a $P_{2U2}$ receptor, or is complementary to nucleic acid sequence encoding a $P_{2U2}$ receptor, or hybridizes to such nucleic acid and remains stably bound to it under stringent conditions, or encodes a polypeptide sharing at least 75% sequence identity, preferably at least 80%, and more preferably at least 85%, with the translated amino acid sequence shown in FIG. 1A–FIG. 1C (SEQ ID NO:1). It is typical at least about 10 nucleotides in length and preferably has $P_{2U2}$ receptor related biological or immunological activity. Specifically contemplated are genomic DNA, cDNA, mRNA and antisense molecules, as well as nucleic acids based on alternative backbone or including alternative bases whether derived from natural sources or synthesized.

"Stringent conditions" are those that (1) employ low ionic strength and high temperature for washing, for example, 0.015 M NaCl, 0.0015 M sodium titrate, 0.1% $NaDodSO_4$ at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

"Isolated" nucleic acid will be nucleic acid that is identified and separated from contaminant nucleic acid encoding other polypeptides from the source of nucleic acid. The nucleic acid may be labeled for diagnostic and probe purposes, using any label known and described in the art as useful in connection with diagnostic assays.

Of particular interest is a $P_{2U2}$ receptor nucleic acid that encodes a full-length molecule, including but not necessarily the native signal sequence thereof. Nucleic acid encoding full-length protein is obtained by screening selected cDNA or genomic libraries using the deduced amino acid sequence disclosed herein for the first time, and, if necessary, using conventional primer extension procedures to secure DNA that is complete at its 5' coding end. Such a clone is readily identified by the presence of a start codon in reading frame with the original sequence.

DNA encoding an amino acid sequence variant of a $P_{2U2}$ receptor is prepared as described below or by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of a $P_{2U2}$ receptor.

Techniques for isolating and manipulating nucleic acids are disclosed for example by the following documents: U.S. Pat. No. 5,030,576, U.S. Pat. No. 5,030,576 and International Patent Publications WO94/11504 and WO93/03162. See, also, Sambrook, et al., "Molecular Cloning: A Laboratory Manual", 2nd Edition, Cold Spring Harbor Press, Cold Spring Harbor, N.Y., 1989, and Ausubel, et al. "Current Protocols in Molecular Biology", Vol. 2, Wiley-Interscience, New York, 1987.

As mentioned above, the availability of the isolated cells providing the $P_{2U2}$ receptor on their surface and the availability of the recombinant DNA encoding the $P_{2U2}$ receptor which permits display and expression of the receptor on host cell surfaces, all makes such cells available as a valuable tool for evaluating the ability of candidate agonists or antagonists to bind to the receptor and thus contribute to the receptor's activation or deactivation. In this manner, the invention is related to assay systems which utilize an isolated or a recombinantly produced $P_{2U2}$ receptor to screen for agonist and antagonist activity of candidate drugs. This assay is especially useful in assuring that these candidate therapeutic agents have the desired effect of either activating or inhibiting the $P_{2U2}$ receptor. Determination of these properties is essential in evaluating the specificity of drugs intended for binding other related receptors.

The host cells are typically animal cells, most typically mammalian cells. In order to be useful in the assays, the cells must have intracellular mechanisms which permit the receptor to be displayed on the cell surface. Particularly useful cells for use in the method of the invention are *Xenopus laevis* frog oocytes, which typically utilize cRNA rather than standard recombinant expression systems proceeding from the DNA encoding the desired protein. Capped RNA (at the 5' end) is typically produced from linearized vectors containing DNA sequences encoding the receptor. The reaction is conducted using RNA polymerase and standard reagents. cRNA is recovered, typically using phenol/chloroform precipitation with ethanol and injected into the oocytes.

The animal host cells expressing the DNA encoding the $P_{2U2}$ receptor or the cRNA-injected oocytes are then cultured to effect the expression of the encoding nucleic acids so as to produce the $P_{2U2}$ receptor display on the cell surface. These cells then are used directly in assays for assessment of a candidate drug to bind, antagonize, or activate the receptor.

One method of evaluating candidates as potential therapeutic agents typically involves a binding assay in which the candidate (such as a peptide or a small organic molecule) would be tested to measure if, or to what extent, it binds the $P_{2U2}$ receptor. Preferably, a mammalian or insect cell line is used to express the $P_{2U2}$ receptor or plasma membrane preparations thereof, will be used in a binding assay. For example, a candidate antagonist competes for binding to the $P_{2U2}$ receptor with either a labeled nucleotide agonist or antagonist. Varying concentrations of the candidate are supplied, along with a constant concentration of the labeled agonist or antagonist. The inhibition of binding of the labeled material can then be measured using established techniques. This measurement is then correlated to determine the amount and potency of the candidate that is bound to the $P_{2U2}$ receptor.

Another method of evaluating candidates for potential therapeutic applications typically involves a functional assay in which the candidate's effect upon cells expressing the recombinant $P_{2U2}$ receptor is measured, rather than simply determining its ability to bind the $P_{2U2}$ receptor. Suitable functional assays include those that measure calcium mobilization ($^{45}Ca$ efflux or measurements of intracellular $Ca^{+2}$ concentration with fluorescent dyes such as fura-2) and voltage clamp, described below.

For example, agonist-induced increases in $^{45}Ca$ release by oocytes expressing cRNA encoding the $P_{2U2}$ receptor or other mammalian recombinant cells producing the $P_{2U2}$ receptor can be measured by the techniques described by Williams, et al., *Proc Natl Acad Sci USA* 85:4939–4943

(1988). Intracellular calcium pools are labeled by incubating groups of 30 oocytes in 300 μl calcium-free modified Barth's solution (MBSH) containing 50 μCi $^{45}CaCl_2$ (10–40 mCi/mg Ca; Amersham) for 4 hours at room temperature. The labeled oocytes or cells are washed, then incubated in MBSH II without antibiotics for 90 minutes. Groups of 5 oocytes are selected and placed in individual wells in a 24-well tissue culture plate containing 0.5 ml/well MBSH II without antibiotics. This medium is removed and replaced with fresh medium every 10 minutes; the harvested medium is analyzed by scintillation counting to determine $^{45}Ca$ released by the oocytes during each 10-minute incubation. The 10-minute incubations are continued until a stable baseline of $^{45}Ca$ release per unit time is achieved. Two additional 10-minute collections are obtained, then test medium including agonist is added and $^{45}Ca$ release determined.

Using the above assay, the ability of a candidate drug to activate the $P_{2U2}$ receptor can be tested directly. In this case, the agonists of the invention are used as controls. In addition, by using the agonists of the invention to activate the recombinant receptor, the effect of the candidate drug on this activation can be tested directly. Cells expressing the nucleic acids encoding the receptor are incubated in the assay in the presence of agonist with and without the candidate compound. A diminution in activation in the presence of the candidate will indicate an antagonist effect. Conversely, the ability of a candidate drug to reverse the antagonist effects of an antagonist of the invention may also be tested.

As indicated above, receptor activation can also be measured by means of the two-electrode voltage clamp assay. In this assay, agonist-induced inward chloride currents are measured in voltage-clamped oocytes that express the $P_{2U2}$ receptor. The technique suitable for use in the instant invention is described by Julius, et al, *Science* 241:558–563 (1988).

The $P_{2U2}$ receptor also has utility in assays for the diagnosis of renal system diseases and disorders by detection, in tissue samples, of aberrant expression of the $P_{2U2}$ receptor.

Another aspect of the invention relates to $P_{2U2}$ receptor agonists that imitate the activated form of the $P_{2U2}$ receptor. These agonists are useful as control reagents in the above-mentioned assays to verify the workability of the assay system. In addition, agonists for the $P_{2U2}$ receptor may exhibit useful effects in vivo in treating kidney disease.

Another aspect of the invention relates to $P_{2U2}$ receptor antagonists that are modified forms of $P_{2U2}$ receptor peptides. Such antagonists bind to the $P_{2U2}$ receptor, but do not activate it, and prevent receptor activation by naturally occurring ligands by blocking their binding to the receptor. Another group of compounds within the scope of the invention, are antagonists of the $P_{2U2}$ receptor ligands, i.e., these are ligand inhibitors. Both these types of antagonists find utility in diminishing or mediating ligand-mediated events such as calcium release. Yet another second group of antagonists includes antibodies designed to bind specific portions of the $P_{2U2}$ receptor protein. In general, these are monoclonal antibody preparations which are highly specific for any desired region of the $P_{2U2}$ receptor. The antibodies, which are explained in greater detail below, are also useful in immunoassays for the receptor protein, for example, in assessing successful expression of the gene in recombinant systems.

In both the agonists and antagonists, a preferred embodiment is that class of compounds having amino acid sequences that are encoded by the $P_{2U2}$ receptor gene. Preferably, the agonists and antagonists have amino acid sequences, in whole or in part, corresponding to the extracellular domains of the $P_{2U2}$ receptor. For example, preferred peptides of the invention correspond, in whole or in part, to either the amino terminus, which is amino acid no 1, methionine (M) to amino acid no 23, lysine (K) (SEQ ID NO:5); ECD I, which is amino acid no 83, tyrosine (Y) to amino acid no 99, arginine (R) (SEQ ID NO:6); ECD II, which is amino acid no 162, asparagine (N) to amino acid no 183, tyrosine(Y) (SEQ ID NO:7); or ECD III, which is amino acid no 257, alanine (A) to amino acid no 276, phenylalanine (F) (SEQ ID NO:8). Also included in the invention are isolated DNA molecules that encode these specific peptides. Accordingly, the invention pertains to isolated DNA molecules encoding human $P_{2U2}$ receptor peptides comprising the amino acid sequence of FIG. 1 from amino acid no 1, methionine to amino acid no 23, lysine (SEQ ID NO:5); from amino acid no 83, tyrosine to amino acid no 99, arginine (SEQ ID NO:6); from amino acid no 162, asparagine to amino acid no 183, tyrosine (SEQ ID NO:7); and from amino acid no 257, alanine to amino acid no 276, phenylalanine (SEQ ID NO:8).

The invention also includes agonists and antagonists that affect receptor function by binding to one of the intracellular (ICD) domains of the receptor. For example, preferred peptides within this aspect of the invention would correspond, in whole or in part, to either ICD I, which is amino acid no 50, phenylalanine (F) to amino acid no 60, isoleucine (I) (SEQ ID NO:11); ICD II, which is amino acid no 120, arginine (R) to amino acid no 141, leucine (L) (SEQ ID NO:12); ICD III, which is amino acid no 208, tyrosine (Y) to amino acid no 233, leucine (L) (SEQ ID NO:13); or to the carboxy terminus, which is amino acid no 301, histidine (H) to amino acid no 334, lysine (K) (SEQ ID NO:14). Also included in the invention are isolated DNA molecules that encode these specific peptides. Accordingly, the invention pertains to isolated DNA molecules encoding human $P_{2U2}$ receptor peptides comprising the amino acid sequence of FIG. 1 from amino acid no 50, phenylalanine to amino acid no 60, isoleucine (SEQ ID NO:11); amino acid no 120, arginine to amino acid no 141, leucine (SEQ ID NO:12); amino acid no 208, tyrosine to amino acid no 233, leucine (SEQ ID NO:13); and amino acid no 301, histidine (H) to amino acid no 334, lysine (K) (SEQ ID NO:14).

Also included are those compounds where one, two, three or more of the amino acid residues are replaced by one which is not encoded genetically. In other purinergic receptors, the third, sixth and seventh transmembrane ("TM") regions have been shown to play a role in ligand binding. See Erb, et al. *JBC* 270:4185–4188 (1995). Accordingly, it is expected that the amino acid sequences of the TM III, TM VI and TM VII regions of the $P_{2U2}$ receptor, in whole or in part, will be particularly useful in designed antibodies or peptides that can bind the receptor and block ligand binding.

The peptide agonists and antagonists of the invention are preferably about 10–100 amino acids in length, more preferably 25–75 amino acids in length. These peptides can be readily prepared using standard solid phase or solution phase peptide synthesis, as is well known in the art. In addition, the DNA encoding these peptides can be synthesized using commercially available oligonucleotide synthesis instrumentation and recombinantly produced using standard recombinant production systems. Production using solid phase peptide synthesis is required when non-gene encoded amino acids are to be included in the peptide.

Another aspect of the invention pertains to antibodies, which have both diagnostic and therapeutic uses. Antibodies are able to act as antagonists or agonists by binding specific regions of the $P_{2U2}$ receptor. The antibodies can be monoclonal or polyclonal, but are preferably monoclonal antibodies that are highly specific for the receptor and can be raised against the whole $P_{2U2}$ receptor or regions thereof. Preferably, the antibodies are obtained by immunization of suitable mammalian subjects (typically rabbit, rat, mouse, goat, human, etc.) with peptides containing as antigenic regions those portions of the $P_{2U2}$ receptor intended to be targeted by the antibodies. Critical regions include any region(s) of proteolytic cleavage, any segment(s) of the extracellular segment critical for activation, and the portions of the sequence which form the extracellular loops. These antibodies also find utility in immunoassays that measure the presence of the $P_{2U2}$ receptor, for example in immunoassays that measure gene expression.

The antibodies of the present invention can be prepared by techniques that are well known in the art. Antibodies are prepared by immunizing suitable mammalian hosts in appropriate immunization protocols using the peptide haptens (immunogen) alone, if they are of sufficient length, or, if desired, or if required to enhance immunogenicity, conjugated to suitable carriers. The immunogen will typically contain a portion of the $P_{2U2}$ receptor that is intended to be targeted by the antibodies. Critical regions include those regions corresponding to the extracellular domains of the $P_{2U2}$ receptor protein. Methods for preparing immunogenic conjugates with carriers such as bovine serum albumin, keyhole limpet hemocyanin, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten can be extended at the amino or carboxy terminus with a cysteine residue or interspersed with cysteine residues, for example, to facilitate linking to carrier. The desired immunogen is administered to a host by injection over a suitable period of time using suitable adjuvants followed by collection of sera. Over the course of the immunization schedule, titers of antibodies are taken to determine the adequacy of antibody formation.

Polyclonal antibodies are suitable for many diagnostic and research purposes and are easily prepared. Monoclonal antibodies are often preferred for therapeutic applications and are prepared by continuous hybrid cell lines and collection of the secreted protein. Immortalized cell lines that secrete the desired monoclonal antibodies can be prepared by the method described in Kohler and Milstein, *Nature* 256:495–497 (1975) or modifications which effect immortalization of lymphocytes or spleen cells, as is generally known. The immortalized cell lines are then screened by immunoassay techniques in which the antigen is the immunogen or a cell expressing the $P_{2U2}$ receptor on its surface. Cells that are found to secrete the desired antibody, can then be cultured in vitro or by production in the ascites fluid. The antibodies are then recovered from the culture supernatant or from the ascites supernatant.

Alternately, antibodies can be prepared by recombinant means, i.e., the cloning and expression of nucleotide sequences or mutagenized versions thereof that at a minimum code for the amino acid sequences required for specific binding of natural antibodies. Antibody regions that bind specifically to the desired regions of receptor can also be produced as chimeras with regions of multiple species origin.

Antibodies may include a complete immunoglobulin or a fragment thereof, and includes the various classes and isotypes such as IgA, IgD, IgE, IgG1, IgG2a, IgG2b, IgG3 and IgM. Fragments include Fab, Fv, F(ab')$_2$, Fab', and so forth. Fragments of the monoclonals or the polyclonal antisera which contain the immunologically significant portion can be used as antagonists, as well as the intact antibodies. Use of immunologically reactive fragments, such as the Fab, Fab', or F(ab')$_2$ fragments is often preferable, especially in a therapeutic context, as these fragments have different immunogenicity than the whole immunoglobulin, and do not carry the biological activity of an immunoglobulin constant domain.

The antibodies thus produced are useful not only as potential agonist or antagonists for the receptor, filling the role of agonist or antagonist in the assays of the invention, but are also useful in immunoassays for detecting the activated receptor. As such these antibodies can be coupled to imaging agents for administration to a subject to allow detection of localized antibody to ascertain the position of $P_{2U2}$ receptors in either activated or unactivated form. In addition, these reagents are useful in vitro to detect, for example, the successful production of the $P_{2U2}$ receptor deployed at the surface of the recombinant host cells.

Yet another aspect of the invention relates to pharmaceutical compositions containing the compounds of the invention. The agonists and antagonists of the invention have therapeutic utility in (1) treating diseases caused by aberrant activation of this receptor in tissues where it is customarily found, for example in the kidney and (2) treating diseases whose symptoms can be ameliorated by stimulating or inhibiting the activity of the $P_{2U2}$ receptor.

The peptide agonists and antagonists of the invention can be administered in conventional formulations for systemic administration such as is well known in the art. Typical formulations may be found, for example, in *Remington's Pharmaceutical Sciences, Mack Publishing Co., Easton Pa., latest edition.*

Preferred forms of systemic administration include injection, typically by intravenous injection. Other injection routes, such as subcutaneous, intramuscular, or intraperitoneal, can also be used. More recently, alternative means for systemic administration of peptides have been devised which include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the patient's condition, and the judgment of the attending physician. Suitable dosage ranges, however, are in the range of 0.1–100 µg/kg of subject. Wide variations in the needed dosage, however, are to be expected in view of the variety of peptides available and the differing efficiencies of various routes of administration. For example, oral administration would be expected to require higher dosages than administration by intravenous injection. Variations in these dosage levels can be adjusted using standard empirical routines for optimization as is well understood in the art.

The invention also relates to the therapeutic, prophylactic and research uses of various techniques to block or modulate the expression of a $P_{2U2}$ receptor by interfering with the transcription of translation of a DNA or RNA molecule encoding the $P_{2U2}$ receptor. This includes a method to inhibit or regulate expression of $P_{2U2}$ receptors in a cell comprising providing to the cell an oligonucleotide molecule which is antisense to, or forms a triple helix with, $P_{2U2}$ receptor-encoding DNA or with DNA regulating expression of $P_{2U2}$ receptor-encoding DNA, in an amount sufficient to inhibit or regulate expression of the $P_{2U2}$ receptors, thereby inhibiting or regulating their expression. Also included is a method to inhibit or regulate expression of $P_{2U2}$ receptors in a subject, comprising administering to the subject an oligonucleotide molecule which is antisense to, or forms a triple helix with, $P_{2U2}$ receptor-encoding DNA or with DNA regulating expression of $P_{2U2}$ receptor-encoding DNA, in an amount sufficient to inhibit or regulate expression of the $P_{2U2}$ receptors in the subject, thereby inhibiting or regulating their expression. The antisense molecule or triple helix-forming molecule in the above methods is preferably a DNA or RNA oligonucleotide. These utilities are described in greater detail below.

The constitutive expression of antisense RNA in cells has been shown to inhibit the expression of about 20 different genes in mammals and plants, and the list continually grows (Hambor, et al., *J. Exp. Med.* 168:1237–1245 (1988); Holt, et al., *Proc. Natl. Acad. Sci.* 83:4794–4798 (1986); Izant, et al., *Cell* 36:1007–1015 (1984); Izant, et al., *Science* 229:345–352 (1985) and De Benedetti, et al., *Proc. Natl. Sci.* 84:658–662 (1987)). Possible mechanisms for the antisense effect are the blockage of translation or prevention of splicing, both of which have been observed in vitro. Interference with splicing allows the use of intron sequences (Munroe, *EMBO. J.* 7:2523–2532 (1988) which should be less conserved and therefore result in greater specificity in inhibiting expression of a protein of one species but not its homologue in another species.

Therapeutic gene regulation is accomplished using the "antisense" approach, in which the function of a target gene in a cell or organism is blocked, by transfection of DNA, preferably an oligonucleotide, encoding antisense RNA which acts specifically to inhibit expression of the particular target gene. The sequence of the antisense DNA is designed to result in a full or preferably partial antisense RNA transcript which is substantially complementary to a segment of the gene or mRNA which it is intended to inhibit. The complementarity must be sufficient so that the antisense RNA can hybridize to the target gene (or mRNA) and inhibit the target gene's function, regardless of whether the action is at the level of splicing, transcription or translation. The degree of inhibition, readily discernible by one of ordinary skill in the art without undue experimentation, must be sufficient to inhibit, or render the cell incapable of expressing, the target gene. One of ordinary skill in the art will recognize that the antisense RNA approach is but one of a number of known mechanisms which can be employed to block specific gene expression.

By the term "antisense" is intended an RNA sequence, as well as a DNA sequence coding therefor, which is sufficiently complementary to a particular mRNA molecule for which the antisense RNA is specific to cause molecular hybridization between the antisense RNA and the mRNA such that translation of the mRNA is inhibited. Such hybridization must occur under in vivo conditions, that is, inside the cell. The action of the antisense RNA results in specific inhibition of gene expression in the cell. (See: Albers, et al., "Molecular Biology Of The Cell", 2nd Ed., Garland Publishing, Inc., New York, N.Y. (1989), in particular, pages 195–196).

The antisense RNA of the present invention may be hybridizable to any of several portions of a target mRNA, including the coding sequence, a 3' or 5' untranslated region, or other intronic sequences. A preferred antisense RNA is that complementary to the human $P_{2U2}$ receptor mRNA. As is readily discernible by one of skill in the art, the minimal amount of homology required by the present invention is that sufficient to result in hybridization to the specific target mRNA and inhibition of its translation or function while not affecting function of other mRNA molecules and the expression of other genes.

Antisense RNA is delivered to a cell by transformation or transfection with a vector into which has been placed DNA encoding the antisense RNA with the appropriate regulatory sequences, including a promoter, to result in expression of the antisense RNA in a host cell.

"Triple helix" or "triplex" approaches involve production of synthetic oligonucleotides which bind to the major groove of a duplex DNA to form a colinear triplex. Such triplex formation can regulate and inhibit cellular growth. See, for example: Hogan, et al., U.S. Pat. No. 5,176,996; Cohen, et al., *Sci. Amer.*, December 1994, p. 76–82; Helene, *Anticancer Drug Design* 6:569–584 (1991); Maher III, et al., *Antisense Res. Devel.* 1:227–281 (Fall 1991); Crook, et al. eds., "Antisense Research and Applications", CRC Press, 1993. It is based in part on the discovery that a DNA oligonucleotide can bind by triplex formation to a duplex DNA target in a gene regulatory region, thereby repressing transcription initiation (Cooney, et. al. *Science* 241:456 (1988)). The present invention utilizes methods such as those of Hogan et al., supra (incorporated herein by reference in its entirety), to designing oligonucleotides which will bind tightly and specifically to a duplex DNA target comprising part of the $P_{2U2}$ receptor-encoding DNA or a regulatory sequence thereof. Such triplex oligonucleotides can therefore be used as a class of drug molecules to selectively manipulate the expression of this gene.

Thus the present invention is directed to providing to a cell or administering to a subject a synthetic oligonucleotide in sufficient quantity for cellular uptake and binding to a DNA duplex of the target $P_{2U2}$ receptor-coding DNA sequence or a regulatory sequence thereof, such that the oligonucleotide binds to the DNA duplex to form a colinear triplex. This method is used to inhibit expression of the receptor on cells in vitro or in vivo. Preferably the target sequence is positioned within the DNA domain adjacent to the RNA transcription origin. This method can also be used to inhibit growth of cells which is dependent on expression of this receptor. The method may also be used to alter the relative amounts or proportions of the $P_{2U2}$ receptor expressed on cells or tissues by administering such a triplex-forming synthetic oligonucleotide.

The following examples are intended to illustrate but not to limit the invention.

EXAMPLE 1

PCR (Polymerase Chain Reaction) Amplification of Related Purinergic Receptor cDNA with Degenerate Primers DAMI cells (obtained from ATCC (#CRL9792)), were cultured in RPMI with 10% fetal bovine serum, plus glutamine, penicillin/streptomycin and kanamycin, in 7% $CO_2$/93% air and mRNA was isolated by the guanidine thiocyanate method. Poly-A(+) mRNA was selected two times using oligo-dT columns (Stratagene). The twice-selected poly-A+ mRNA was used to generate first-strand cDNA by priming with either oligo-dT or random primers and AMV reverse transcriptase (Invitrogen) as a template for PCR. Primers were designed based on the sequence of transmembrane region 3 (TM III, primer 3B) and transmembrane region 7 (TM VII, primer 7A2) from the mouse $P_{2U}$ (Lustig, et al, *Proc. Natl. Acad. Sci., USA* 90:5113–5117 (1993)) and the chicken $P_2Y_1$ (Webb, et al, *FEBS Letters* 324:219–225 (1993)) receptor. The nucleotide sequence of 3B (SEQ ID NO:9) was:

5'AT(CT)CT(GTC)TT(CT)CTGAC(CTA)TG(CT)AT(C-T)(AT)(GC)IGT(GTC)CA 3' and the sequence for 7A2 (SEQ ID NO:10) was:

3'GG(GAT)(TC)A(CGA)(GA)AIAT(GA)AA(AG)(GA)AICGICC5' where G is guanine, C is cytosine, A is adenine, T is thymidine and I is inosine, and the "( )" indicate positions of degeneracy such that the sequences were a mixture with the indicated substitutions at that given position. The following conditions were used for PCR using Taq polymerase: 5 cycles of 93° C., 2 minutes; 60° C., 1.5 minutes; 72° C., 2.5 minutes; 5 cycles of 93° C., 2 minutes; 55° C., 1.5 minutes; 72° C., 2.5 minutes; 25 cycles of 93° C., 2 minutes; 50° C., 1.5 minutes; 72° C., 2.5 minutes, followed by a final extension of 72° C., 5 min. PCR products were purified over a size-selection column and ligated directly into the pCR2 TA cloning vector (Invitrogen) and the DNA was used to transform DH5α strain of *E. coli*. Colonies were selected and DNA was prepared for restriction analysis and sequencing. Cycle sequencing was performed using Taq polymerase and dye-terminator mixes (Perkin-Elmer/ABI) and the results were analyzed on an ABI 373 automatic sequencer. Sequence results obtained with one clone, called 206.18, exhibited homology with published purinergic receptor sequences.

EXAMPLE 2

Isolation of Full-length Human cDNA encoding $P_{2U2}$

Insert was isolated from the PCR clone of interest (206.18), purified from an agarose gel, radiolabeled with [α-$^{32}$P]dCTP(NEN) by random-priming (Stratagene), and used to screen a DAMI cDNA library in λgt22. The library was generated using twice-selected poly-A+ mRNA (see above) and first strand cDNA synthesis was primed with an oligo-dT primer and synthesized with Moloney murine leukemia virus (M-MLV) reverse transcriptase (Gibco/BRL). CDNA was directionally ligated into the SalI/NotI sites of the λgt22 arms and packaged (Stratagene packaging extract) and amplified in the Y1090 (r-) strain. One million clones were screened at a density of 40,000/plate under the following conditions: duplicate nitrocellulose filters (S&S) were hybridized overnight at 42° C. in a solution containing 50% deionized formamide, 5×SSC (sodium chloride, sodium citrate), 0.1 mg/ml heat denatured salmon sperm DNA, 0.1% sodium dodecylsulfate, 1×Denhardt's, 0.02M Tris, pH 7.5 and 1–2×106 cpm/ml of radiolabeled probe. Filters were washed twice at room temperature for 10 minutes in 0.1% sodium dodecylsulfate, 2×SSC and then at 55° C. for 30 minutes in 0.2×SSC, 0.1% sodium dodecylsulfate, then exposed with an intensifying screen overnight at –70° C. with Kodak XAR film. Positively hybridizing clones were plaque purified, λ DNA was prepared and the cDNA inserts were excised and subcloned into the commercially available pBluescript vector. The hybridizing and adjacent regions were sequenced on both strands as above on an ABI 373 automatic sequencer.

Figure 2:
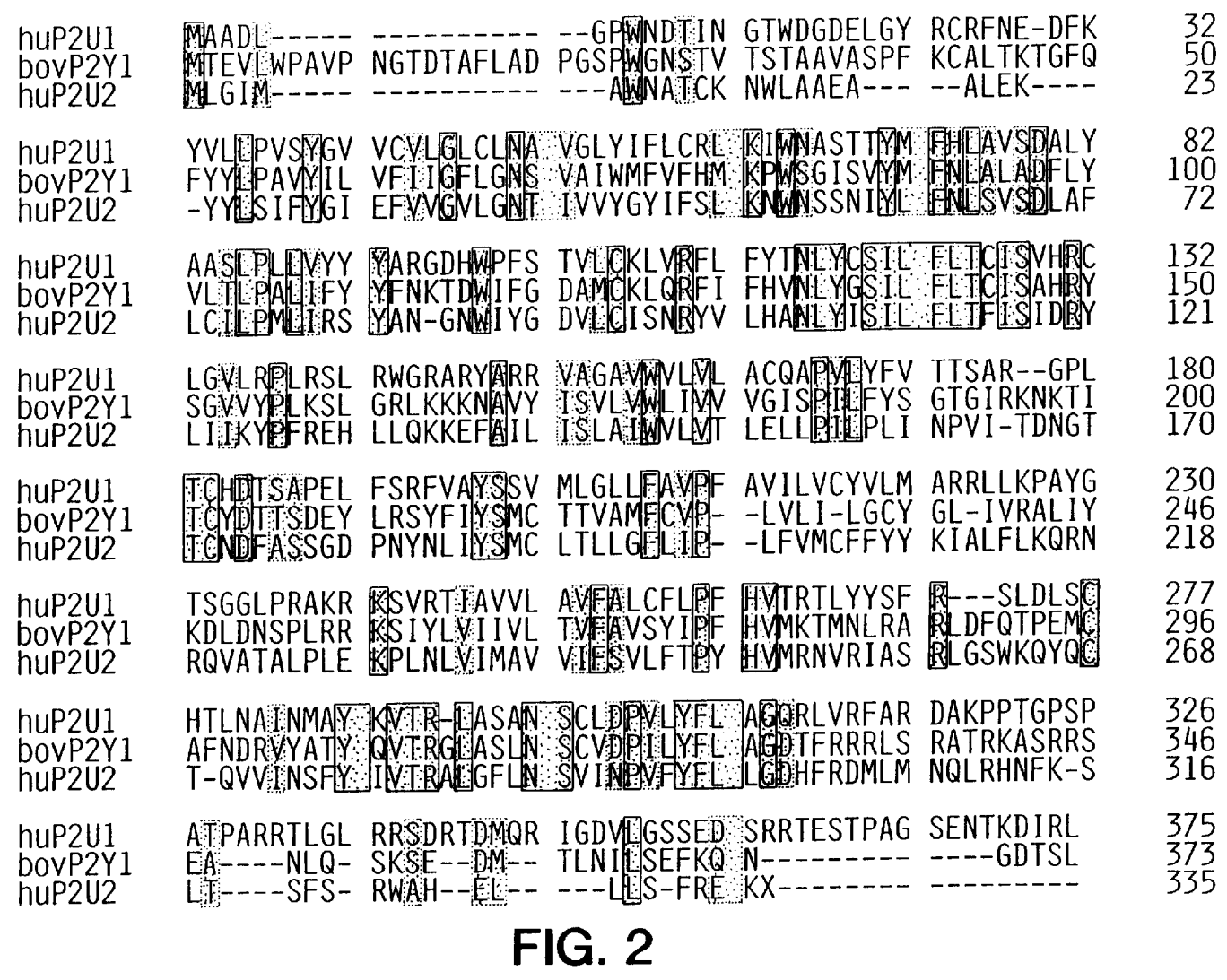

To isolate additional 5' sequence for the $P_{2U2}$ gene, a 5' proximal fragment from the largest DAMI clone (D8) was used to screen a Clontech human kidney cDNA library (λgt10) under identical screening conditions as were used for the DAMI cDNA library. DNA from plaque-purified positively hybridizing clones from both libraries were analyzed by restriction digest. Inserts from clones of interest were excised and subcloned into the commercially available pBluescript vector and sequenced as above. The complete open reading frame as well as truncated versions of the full-length CDNA were cloned into Xenopus oocyte or mammalian expression vectors for functional analysis. The DNA sequence of the complete open reading frame for the longest cDNA isolated from the kidney cDNA library is shown in FIG. 1 (SEQ ID NO:1). As shown in FIG. 2, the deduced amino acid sequence of the $P_{2U2}$ cDNA shows extensive homology with other known purinergic receptors (Parr, supra, and Henderson, supra).

EXAMPLE 3

Expression of $P_{2U2}$ mRNA in Various Tissues and Cell Lines

Poly-(A)+ RNA was isolated from a variety of cell lines as described above. Five μg of each sample was denatured, electrophoresed on a 1.2% formaldehyde agarose gel, and transferred to nylon membrane. Blots were probed with [α-$^{32}$P]dCTP(NEN) labeled insert, as described for the library screenings, and hybridized at 42° C. overnight in the following solution: 5×SSPE, 1×Denhardt's, 50% formamide, 2% sodium dodecylsulfate, 0.1 mg/ml heat denatured salmon sperm DNA. Blots were washed twice at room temperature for 15 minutes in 0.05% SDS, 2×SSC and then at 50° C. for 30 minutes in 0.1×SSC, 0.1% SDS and exposed at –70° C. to Kodak XAR film for 48–72 hours with an intensifying screen. Northern blots containing poly-A+ RNA from human tissues were purchased from Clontech and hybridized, washed and exposed as described above. Hybridization of RNA tissue blots with the labeled $P_{2U2}$ DNA fragment demonstrated that a 4.4 kB mRNA is abundantly expressed in human kidney, but is negative for other tissues examined (heart, brain, placenta, lung, liver, skeletal muscle, pancreas, spleen, thymus, prostate, testis, ovary, small intestine, colon and peripheral blood leukocytes). These results distinguish this receptor from other reported purinergic receptors since these other receptors are abundant in brain. A series of mRNAs isolated from a variety of human hematopoietic and lymphocytic cell lines were used in a Northern analysis and a 4.4 kB message for the receptor was demonstrated to be abundant in several cell lines of erythroleukemic (HEL, K562) and megakaryocytic (DAMI) origin, and not present in the monocytic cell line U937 or the T-cell derived Jurkat cell line.

EXAMPLE 4

Demonstration of the Function of the Receptor in Oocytes

The native human receptor was produced in oocytes by cloning the 500 bp 5' truncation of the full-length kidney cDNA clone into the mammalian expression vector pcDNA3 (Invitrogen). Linearized DNA was used as a template for T7 polymerase (Ambion, Promega) for generation of capped in vitro transcribed mRNA following the supplier's specifications. Adult female *Xenopus laevis* were anesthetized in [0.015 g/l] 3-aminobenzoic acid ethyl ester for 10 minutes and 1 or 2 ovarian lobes were removed, followed by immediate suturing of the incisions. Oocytes were defolliculated at room temperature with collagenase (2 mg/ml) in $Ca^{+2}$-free medium (OR-2) for 1–2 hr. Oocytes were stored at 18° C. in ND-96 (96 mM sodium chloride, 2 mM potassium chloride, 1.8 mM calcium chloride, 1 mM magnesium chloride, 5 mM HEPES (N[2-hydroxyethylpiperazine-N'[2-ethanesulfonic acid) with penicillin/streptomycin and injected with 50 nl RNA (1–2 μg/μl) 18–24 h after removal of the oocytes. Before recording, injected oocytes were stored at 18° C. for 2–3 days with daily media changes.

A two-electrode voltage clamp (Axon Axoclamp2B) was used to measure agonist-induced currents from individual oocytes. Electrodes were pulled to resistances of 0.2–1MΩ and filled with 3M KCl. Recordings were made at room temperature in ND96 from oocytes clamped at −70 mV using different agonist concentrations. Water-injected oocytes were used as a control. FIG. 3 shows representative chloride currents obtained from oocytes injected with cRNA for the $P_{2U2}$ receptor and challenged with a variety of purinergic agonists (ADP, ATP, UTP, UDP).

All references cited and mentioned above, including patents, journal articles and texts, are all incorporated by reference herein, whether expressly incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

We claim:

1. A method to determine whether a candidate compound activates or inhibits a $P_{2U2}$ receptor, comprising the steps of:
providing a host cell transformed or injected with a nucleic acid molecule which encodes a $P_{2U2}$ receptor and which hybridizes to the complement of a nucleic acid molecule having SEQ ID NO:1 under conditions selected from the group consisting of: (1) washing with 0.015 M NaCl, 0.0015 M sodium titrate, 0.1% NaDodSO$_4$ at 50° C.; (2) hybridization in 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; and (3) hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS, whereby said host cell expresses on its surface a $P_{2U2}$ receptor;
contacting said host cell with the candidate compound;
measuring the compound's effect on the $P_{2U2}$ receptor expressed by the host cell;
comparing the compound's effect on the $P_{2U2}$ receptor to the compound's effect on a control cell; and
determining whether the compound activates or inhibits the $P_{2U2}$ receptor expressed by said encoding nucleic acid molecule, wherein said $P_{2U2}$ receptor is activated by four agonists in the following order of specificity: UTP>UDP>ADP>ATP in *Xenopus laevis* oocytes.

2. The method of claim 1, in which the step of measuring the compound's effect on the $P_{2U2}$ receptor comprises the measurement of calcium ion mobilization or inward chloride currents.

3. The method of claim 2, wherein said inward chloride currents are measured using a voltage clamp.

4. The method of claim 1, in which said host cell is selected from the group consisting of mammalian cells, *Xenopus laevis* oocytes and insect cells.

5. A method of screening for a candidate compound which binds to a $P_{2U2}$ receptor comprising the steps of:
providing a host cell transformed with the complement of a nucleic acid molecule which encodes a $P_{2U2}$ receptor and which hybridizes to a nucleic acid molecule having SEQ ID NO:1 under conditions selected from the group consisting of: (1) washing with 0.015 M NaCl, 0.0015 M sodium titrate, 0.1% NaDodSO$_4$ at 50° C.; (2) hybridization in 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; and (3) hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS, whereby said host cell expresses on its surface a $P_{2U2}$ receptor;

contacting said host cell with the candidate compound;

measuring the binding of the compound to the $P_{2U2}$ receptor expressed by the host cell;

comparing the compound's binding to the $P_{2U2}$ receptor to the compound's binding to a control cell; and determining whether the candidate compound binds to the $P_{2U2}$ receptor expressed by said encoding nucleic acid molecule, wherein said $P_{2U2}$ receptor is activated by four agonists in the following order of specificity: UTP>UDP>ADP>ATP in *Xenopus laevis* oocytes.

6. The method of claim 5, wherein the contacting of the host cell with the candidate compound is in the presence of a labeled ligand known to bind to the $P_{2U2}$ receptor so that the candidate compound competes with the labeled ligand known to bind to the $P_{2U2}$ receptor.

7. The method of claim 5, wherein the candidate compound is a $P_{2U2}$ receptor peptide.

8. The method of claim 5, wherein the candidate compound is an antibody.

9. The method of either of claims 1 or 5, wherein the $P_{2U2}$ receptor comprises the amino acid sequence of SEQ ID No: 2.

10. The method of either of claims 1 or 5 wherein the $P_{2U2}$ receptor consists of the amino acid sequence of SEQ ID No: 2.

11. The method of either of claims 1 or 5, wherein the nucleic acid molecule comprises SEQ ID NO:1.

12. The method of either of claims 1 or 5, wherein the nucleic acid molecule comprises nucleotides 625–1626 of SEQ ID NO:1.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 1996 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 625..1626

(xi) SEQUENCE DESCRIPTION: SEQ ID NO:1:

```
ATAAAGTATG TTTAGCCCTC ATGTCACATG AACCTTTATG CATTGAAGAT TGTTTCCCTT    60

GCCCCCCCAG GGGGTGGGGT TATTTTTCTA TCCTTGTTAA CTTCCCTATA TTATTATATA   120

CACTTTGAGT TTTAGGGTAC ATGTGCACAA AGTGCAGGTT AGTTACATAT GTATACATGT   180

GCCATGTTGG TGTGCTGCAC CCATTAACAC ATCATTTAGC ATGAGGTATA TCTCCTAATG   240

TTATCCCTCC CCCCTCCCCC CACCCCACAA CAGTCCCCGG AGTGTGATAT TCCCCTTTCC   300

TGTGTCCATG TGTTATTATT CCAATTCCCC ACCTATGAAG TGAAAATATG CAGGTGTTTG   360

GATTTTTGTC CTTGGCAATA GTTTTGCTGA GAATGATGGT TTCCAGCTTC ATCCATGTCC   420

CTACAAAGGA CATGAACTCA TCATTTTTTA TGACTGCATA GTATTCTATG GTGTATACAT   480

GCCAACTTTT CTCCCCCCCC TTTTTAAGCT CCTTCTTTCA CTGGCTTTCA TGATCCCACC   540

AATTCCTGCT TTTCCTTTTT TGTTTTTTTC TTCCAACAGA ATGGTTATGG TTTAACTCAG   600

CAGAATTTGT TGAACAACTA CGAC ATG CTG GGG ATC ATG GCA TGG AAT GCA    651
                         Met Leu Gly Ile Met Ala Trp Asn Ala
                          1               5

ACT TGC AAA AAC TGG CTG GCA GCA GAG GCT GCC CTG GAA AAG TAC TAC    699
Thr Cys Lys Asn Trp Leu Ala Ala Glu Ala Ala Leu Glu Lys Tyr Tyr
 10              15                  20                  25

CTT TCC ATT TTT TAT GGG ATT GAG TTC GTT GTG GGA GTC CTT GGA AAT    747
```

```
                                                      -continued

Leu Ser Ile Phe Tyr Gly Ile Glu Phe Val Gly Val Leu Gly Asn
             30                  35                  40

ACC ATT GTT GTT TAC GGC TAC ATC TTC TCT CTG AAG AAC TGG AAC AGC        795
Thr Ile Val Val Tyr Gly Tyr Ile Phe Ser Leu Lys Asn Trp Asn Ser
             45                  50                  55

AGT AAT ATT TAT CTC TTT AAC CTC TCT GTC TCT GAC TTA GCT TTT CTG        843
Ser Asn Ile Tyr Leu Phe Asn Leu Ser Val Ser Asp Leu Ala Phe Leu
             60                  65                  70

TGC ACC CTC CCC ATG CTG ATA AGG AGT TAT GCC AAT GGA AAC TGG ATA        891
Cys Thr Leu Pro Met Leu Ile Arg Ser Tyr Ala Asn Gly Asn Trp Ile
 75                  80                  85

TAT GGA GAC GTG CTC TGC ATA AGC AAC CGA TAT GTG CTT CAT GCC AAC        939
Tyr Gly Asp Val Leu Cys Ile Ser Asn Arg Tyr Val Leu His Ala Asn
 90                  95                 100                 105

CTC TAT ACC AGC ATT CTC TTT CTC ACT TTT ATC AGC ATA GAT CGA TAC        987
Leu Tyr Thr Ser Ile Leu Phe Leu Thr Phe Ile Ser Ile Asp Arg Tyr
                    110                 115                 120

TTG ATA ATT AAG TAT CCT TTC CGA GAA CAC CTT CTG CAA AAG AAA GAG       1035
Leu Ile Ile Lys Tyr Pro Phe Arg Glu His Leu Leu Gln Lys Lys Glu
            125                 130                 135

TTT GCT ATT TTA ATC TCC TTG GCC ATT TGG GTT TTA GTA ACC TTA GAG       1083
Phe Ala Ile Leu Ile Ser Leu Ala Ile Trp Val Leu Val Thr Leu Glu
            140                 145                 150

TTA CTA CCC ATA CTT CCC CTT ATA AAT CCT GTT ATA ACT GAC AAT GGC       1131
Leu Leu Pro Ile Leu Pro Leu Ile Asn Pro Val Ile Thr Asp Asn Gly
 155                 160                 165

ACC ACC TGT AAT GAT TTT GCA AGT TCT GGA GAC CCC AAC TAC AAC CTC       1179
Thr Thr Cys Asn Asp Phe Ala Ser Ser Gly Asp Pro Asn Tyr Asn Leu
 170                 175                 180                 185

ATT TAC AGC ATG TGT CTA ACA CTG TTG GGG TTC CTT ATT CCT CTT TTT       1227
Ile Tyr Ser Met Cys Leu Thr Leu Leu Gly Phe Leu Ile Pro Leu Phe
            190                 195                 200

GTG ATG TGT TTC TTT TAT TAC AAG ATT GCT CTC TTC CTA AAG CAG AGG       1275
Val Met Cys Phe Phe Tyr Tyr Lys Ile Ala Leu Phe Leu Lys Gln Arg
            205                 210                 215

AAT AGG CAG GTT GCT ACT GCT CTG CCC CTT GAA AAG CCT CTC AAC TTG       1323
Asn Arg Gln Val Ala Thr Ala Leu Pro Leu Glu Lys Pro Leu Asn Leu
            220                 225                 230

GTC ATC ATG GCA GTG GTA ATC TTC TCT GTG CTT TTT ACA CCC TAT CAC       1371
Val Ile Met Ala Val Val Ile Phe Ser Val Leu Phe Thr Pro Tyr His
 235                 240                 245

GTC ATG CGG AAT GTG AGG ATC GCT TCA CGC CTG GGG AGT TGG AAG CAG       1419
Val Met Arg Asn Val Arg Ile Ala Ser Arg Leu Gly Ser Trp Lys Gln
 250                 255                 260                 265

TAT CAG TGC ACT CAG GTC GTC ATC AAC TCC TTT TAC ATT GTG ACA CGG       1467
Tyr Gln Cys Thr Gln Val Val Ile Asn Ser Phe Tyr Ile Val Thr Arg
            270                 275                 280

GCT TTG GGC TTT CTG AAC AGT GTC ATC AAC CCT GTC TTC TAT TTT CTT       1515
Ala Leu Gly Phe Leu Asn Ser Val Ile Asn Pro Val Phe Tyr Phe Leu
            285                 290                 295

TTG GGA GAT CAC TTC AGG GAC ATG CTG ATG AAT CAA CTG AGA CAC AAC       1563
Leu Gly Asp His Phe Arg Asp Met Leu Met Asn Gln Leu Arg His Asn
            300                 305                 310

TTC AAA TCC CTT ACA TCC TTT AGC AGA TGG GCT CAT GAA CTC CTA CTT       1611
Phe Lys Ser Leu Thr Ser Phe Ser Arg Trp Ala His Glu Leu Leu Leu
 315                 320                 325

TCA TTC AGA GAA AAG TGAGGGGCTT GTGAAACAGA TTGTTCTACA GATGAATCTG       1666
Ser Phe Arg Glu Lys
 330
```

```
TAAGCCAGTT ACAGTTTGCT TTAACTCATA GACATCAATC AGAGAGTGTC ACAGATTTAA    1726

CCTTGATCTA AAGACAAGTT GTACCCAGAG TATGTGAAAA GAATGGGACG ACAAGAATGT    1786

ACTGGTTTCT TCCTCTAAGA ATTGAAAGGA GTTGAACTGC CTTATGTTTG GGCATGTAAC    1846

TCCAAAATAC TAGGTAGTAT AAGGCTTTCT CAATCAGTCC CCAAATGGAA GATATATAAA    1906

GCAACAAGTT GTCTGCATTT GATCACTGGT CAGATTGTAA AAAAAAAAAA AAAAAAGGGC    1966

GCCCGCCACC GCGGTGGAGC TCCAATCGCC                                     1996
```

(2) INFORMATION FOR SEQ ID NO:2:

(i) SEQUENCE CHARACTERISTICS:
        (A) LENGTH: 334 amino acids
        (B) TYPE: amino acid
        (D) TOPOLOGY: linear (ii) MOLECULE TYPE: protein (xi) SEQUENCE DESCRIPTION: SEQ ID NO:2:

```
Met Leu Gly Ile Met Ala Trp Asn Ala Thr Cys Lys Asn Trp Leu Ala
 1               5                  10                  15

Ala Glu Ala Ala Leu Glu Lys Tyr Tyr Leu Ser Ile Phe Tyr Gly Ile
                20                  25                  30

Glu Phe Val Val Gly Val Leu Gly Asn Thr Ile Val Tyr Gly Tyr
            35                  40                  45

Ile Phe Ser Leu Lys Asn Trp Asn Ser Ser Asn Ile Tyr Leu Phe Asn
        50                  55                  60

Leu Ser Val Ser Asp Leu Ala Phe Leu Cys Thr Leu Pro Met Leu Ile
65                  70                  75                  80

Arg Ser Tyr Ala Asn Gly Asn Trp Ile Tyr Gly Asp Val Leu Cys Ile
                85                  90                  95

Ser Asn Arg Tyr Val Leu His Ala Asn Leu Tyr Thr Ser Ile Leu Phe
            100                 105                 110

Leu Thr Phe Ile Ser Ile Asp Arg Tyr Leu Ile Ile Lys Tyr Pro Phe
        115                 120                 125

Arg Glu His Leu Leu Gln Lys Lys Glu Phe Ala Ile Leu Ile Ser Leu
    130                 135                 140

Ala Ile Trp Val Leu Val Thr Leu Glu Leu Leu Pro Ile Leu Pro Leu
145                 150                 155                 160

Ile Asn Pro Val Ile Thr Asp Asn Gly Thr Thr Cys Asn Asp Phe Ala
                165                 170                 175

Ser Ser Gly Asp Pro Asn Tyr Asn Leu Ile Tyr Ser Met Cys Leu Thr
            180                 185                 190

Leu Leu Gly Phe Leu Ile Pro Leu Phe Val Met Cys Phe Phe Tyr Tyr
        195                 200                 205

Lys Ile Ala Leu Phe Leu Lys Gln Arg Asn Arg Gln Val Ala Thr Ala
    210                 215                 220

Leu Pro Leu Glu Lys Pro Leu Asn Leu Val Ile Met Ala Val Val Ile
225                 230                 235                 240

Phe Ser Val Leu Phe Thr Pro Tyr His Val Met Arg Asn Val Arg Ile
                245                 250                 255

Ala Ser Arg Leu Gly Ser Trp Lys Gln Tyr Gln Cys Thr Gln Val Val
            260                 265                 270

Ile Asn Ser Phe Tyr Ile Val Thr Arg Ala Leu Gly Phe Leu Asn Ser
        275                 280                 285

Val Ile Asn Pro Val Phe Tyr Phe Leu Leu Gly Asp His Phe Arg Asp
```

```
            290                 295                 300
Met Leu Met Asn Gln Leu Arg His Asn Phe Lys Ser Leu Thr Ser Phe
305                 310                 315                 320

Ser Arg Trp Ala His Glu Leu Leu Leu Ser Phe Arg Glu Lys
                325                 330
```

(2) INFORMATION FOR SEQ ID NO:3:

(i) SEQUENCE CHARACTERISTICS:
        (A) LENGTH: 375 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

```
Met Ala Ala Asp Leu Gly Pro Trp Asn Asp Thr Ile Asn Gly Thr Trp
1               5                   10                  15

Asp Gly Asp Glu Leu Gly Tyr Arg Cys Arg Phe Asn Glu Asp Phe Lys
                20                  25                  30

Tyr Val Leu Leu Pro Val Ser Tyr Gly Val Val Cys Val Leu Gly Leu
            35                  40                  45

Cys Leu Asn Ala Val Gly Leu Tyr Ile Phe Leu Cys Arg Leu Lys Thr
50                  55                  60

Trp Asn Ala Ser Thr Thr Tyr Met Phe His Leu Ala Val Ser Asp Ala
65                  70                  75                  80

Leu Tyr Ala Ala Ser Leu Pro Leu Leu Val Tyr Tyr Ala Arg Gly
                85                  90                  95

Asp His Trp Pro Phe Ser Thr Val Leu Cys Lys Leu Val Arg Phe Leu
                100                 105                 110

Phe Tyr Thr Asn Leu Tyr Cys Ser Ile Leu Phe Leu Thr Cys Ile Ser
            115                 120                 125

Val His Arg Cys Leu Gly Val Leu Arg Pro Leu Arg Ser Leu Arg Trp
130                 135                 140

Gly Arg Ala Arg Tyr Ala Arg Arg Val Ala Gly Ala Val Trp Val Leu
145                 150                 155                 160

Val Leu Ala Cys Gln Ala Pro Val Leu Tyr Phe Val Thr Thr Ser Ala
                165                 170                 175

Arg Gly Pro Leu Thr Cys His Asp Thr Ser Ala Pro Glu Leu Phe Ser
            180                 185                 190

Arg Phe Val Ala Tyr Ser Ser Val Met Leu Gly Leu Leu Phe Ala Val
            195                 200                 205

Pro Phe Ala Val Ile Leu Val Cys Tyr Val Leu Met Ala Arg Arg Leu
210                 215                 220

Leu Lys Pro Ala Tyr Gly Thr Ser Gly Gly Leu Pro Arg Ala Lys Arg
225                 230                 235                 240

Lys Ser Val Arg Thr Ile Ala Val Val Leu Ala Val Phe Ala Leu Cys
                245                 250                 255

Phe Leu Pro Phe His Val Thr Arg Thr Leu Tyr Tyr Ser Phe Arg Ser
                260                 265                 270

Leu Asp Leu Ser Cys His Thr Leu Asn Ala Ile Asn Met Ala Tyr Lys
            275                 280                 285

Val Thr Arg Leu Ala Ser Ala Asn Ser Cys Leu Asp Pro Val Leu Tyr
            290                 295                 300

Phe Leu Ala Gly Gln Arg Leu Val Arg Phe Ala Arg Asp Ala Lys Pro
```

```
305                 310                 315                 320
Pro Thr Gly Pro Ser Pro Ala Thr Pro Ala Arg Arg Thr Leu Gly Leu
                325                 330                 335

Arg Arg Ser Asp Arg Thr Asp Met Gln Arg Ile Gly Asp Val Leu Gly
                340                 345                 350

Ser Ser Glu Asp Ser Arg Arg Thr Glu Ser Thr Pro Ala Gly Ser Glu
                355                 360                 365

Asn Thr Lys Asp Ile Arg Leu
                370                 375

(2) INFORMATION FOR SEQ ID NO:4:

(i) SEQUENCE CHARACTERISTICS:
         (A) LENGTH: 373 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO:4:

Met Thr Glu Val Leu Trp Pro Ala Val Pro Asn Gly Thr Asp Thr Ala
1               5                   10                  15

Phe Leu Ala Asp Pro Gly Ser Pro Trp Gly Asn Ser Thr Val Thr Ser
                20                  25                  30

Thr Ala Val Ala Ser Pro Phe Lys Cys Ala Leu Thr Lys Thr Gly
                35                  40                  45

Phe Gln Phe Tyr Tyr Leu Pro Ala Val Tyr Ile Leu Val Phe Ile Ile
    50                  55                  60

Gly Phe Leu Gly Asn Ser Val Ala Ile Trp Met Phe Val Phe His Met
65                  70                  75                  80

Lys Pro Trp Ser Gly Ile Ser Val Tyr Met Phe Asn Leu Ala Leu Ala
                85                  90                  95

Asp Phe Leu Tyr Val Leu Thr Leu Pro Ala Leu Ile Phe Tyr Tyr Phe
                100                 105                 110

Asn Lys Thr Asp Trp Ile Phe Gly Asp Ala Met Cys Lys Leu Gln Arg
                115                 120                 125

Phe Ile Phe His Val Asn Leu Tyr Gly Ser Ile Leu Phe Leu Thr Cys
    130                 135                 140

Ile Ser Ala His Arg Tyr Ser Gly Val Val Tyr Pro Leu Lys Ser Leu
145                 150                 155                 160

Gly Arg Leu Lys Lys Lys Asn Ala Val Tyr Ile Ser Val Leu Val Trp
                165                 170                 175

Leu Ile Val Val Val Gly Ile Ser Pro Ile Leu Phe Tyr Ser Gly Thr
                180                 185                 190

Gly Ile Arg Lys Asn Lys Thr Ile Thr Cys Tyr Asp Thr Thr Ser Asp
                195                 200                 205

Glu Tyr Leu Arg Ser Tyr Phe Ile Tyr Ser Met Cys Thr Thr Val Ala
    210                 215                 220

Met Phe Cys Val Pro Leu Val Leu Ile Leu Gly Cys Tyr Gly Leu Ile
225                 230                 235                 240

Val Arg Ala Leu Ile Tyr Lys Asp Leu Asp Asn Ser Pro Leu Arg Arg
                245                 250                 255

Lys Ser Ile Tyr Leu Val Ile Ile Val Leu Thr Val Phe Ala Val Ser
                260                 265                 270

Tyr Ile Pro Phe His Val Met Lys Thr Met Asn Leu Arg Ala Arg Leu
```

```
            275                 280                 285
Asp Phe Gln Thr Pro Glu Met Cys Ala Phe Asn Asp Arg Val Tyr Ala
    290                 295                 300

Thr Tyr Gln Val Thr Arg Gly Leu Ala Ser Leu Asn Ser Cys Val Asp
305                 310                 315                 320

Pro Ile Leu Tyr Phe Leu Ala Gly Asp Thr Phe Arg Arg Leu Ser
                325                 330                 335

Arg Ala Thr Arg Lys Ala Ser Arg Arg Ser Glu Ala Asn Leu Gln Ser
                340                 345                 350

Lys Ser Glu Asp Met Thr Leu Asn Ile Leu Ser Glu Phe Lys Gln Asn
                355                 360                 365

Gly Asp Thr Ser Leu
    370
```

(2) INFORMATION FOR SEQ ID NO:5:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Met Leu Gly Ile Met Ala Trp Asn Ala Thr Cys Lys Asn Trp Leu Ala
1               5                   10                  15

Ala Glu Ala Ala Leu Glu Lys
            20
```

(2) INFORMATION FOR SEQ ID NO:6:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

```
Tyr Ala Asn Gly Asn Trp Ile Tyr Gly Asp Val Leu Cys Ile Ser Asn
1               5                   10                  15

Arg
```

(2) INFORMATION FOR SEQ ID NO:7:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

```
Asn Pro Val Ile Thr Asp Asn Gly Thr Thr Cys Asn Asp Phe Ala Ser
1               5                   10                  15

Ser Gly Asp Pro Asn Tyr
            20
```

(2) INFORMATION FOR SEQ ID NO:8:

(i) SEQUENCE CHARACTERISTICS:
         (A) LENGTH: 20 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:8:

Ala Ser Arg Leu Gly Ser Trp Lys Gln Tyr Gln Cys Thr Gln Val Val
1               5                  10                  15

Ile Asn Ser Phe
            20

(2) INFORMATION FOR SEQ ID NO:9:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(xi) SEQUENCE DESCRIPTION: SEQ ID NO:9:

ATYCTBTTYC TGACHTGYAT YWSNGTBCA                                          29

(2) INFORMATION FOR SEQ ID NO:10:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(xi) SEQUENCE DESCRIPTION: SEQ ID NO:10:

CCNGCNARRA ARTANARVAY DGG                                                23

(2) INFORMATION FOR SEQ ID NO:11:

(i) SEQUENCE CHARACTERISTICS:
         (A) LENGTH: 11 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:11:

Phe Ser Leu Lys Asn Trp Asn Ser Ser Asn Ile
1               5                  10

(2) INFORMATION FOR SEQ ID NO:12:

(i) SEQUENCE CHARACTERISTICS:
         (A) LENGTH: 22 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:12:

Arg Tyr Leu Ile Ile Lys Tyr Pro Phe Arg Glu His Leu Leu Gln Lys
1               5                  10                  15

-continued

```
Lys Glu Phe Ala Ile Leu
            20

(2) INFORMATION FOR SEQ ID NO:13:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Tyr Lys Ile Ala Leu Phe Leu Lys Gln Arg Asn Arg Gln Val Ala Thr
1               5                   10                  15

Ala Leu Pro Leu Glu Lys Pro Leu Asn Leu
            20                  25

(2) INFORMATION FOR SEQ ID NO:14:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

His Phe Arg Asp Met Leu Met Asn Gln Leu Arg His Asn Phe Lys Ser
1               5                   10                  15

Leu Thr Ser Phe Ser Arg Trp Ala His Glu Leu Leu Leu Ser Phe Arg
            20                  25                  30

Glu Lys
```